United States Patent
Tishutin et al.

(10) Patent No.: US 10,314,544 B2
(45) Date of Patent: Jun. 11, 2019

(54) METHOD, APPARATUS AND COMPUTER PROGRAM FOR ACTIVITY SENSOR DATA PROCESSING

(71) Applicant: Nokia Technologies Oy, Espoo (FI)

(72) Inventors: Oleg Tishutin, Moscow (RU); Marc James Ashton Bailey, Cambridge (GB)

(73) Assignee: NOKIA TECHNOLOGIES OY, Espoo (FI)

( * ) Notice: Subject to any disclaimer, the term of this patent is extended or adjusted under 35 U.S.C. 154(b) by 381 days.

(21) Appl. No.: 14/828,282

(22) Filed: Aug. 17, 2015

(65) Prior Publication Data
US 2016/0051199 A1    Feb. 25, 2016

(30) Foreign Application Priority Data

Aug. 19, 2014    (RU) ................................ 2014133946

(51) Int. Cl.
| | | |
|---|---|---|
| *A61B 5/145* | (2006.01) | |
| *A61B 5/00* | (2006.01) | |
| *G06F 9/48* | (2006.01) | |
| *H04L 29/08* | (2006.01) | |

(52) U.S. Cl.
CPC .......... *A61B 5/6898* (2013.01); *G06F 9/4843* (2013.01); *H04L 67/10* (2013.01); *H04L 67/12* (2013.01)

(58) Field of Classification Search
CPC ....... A61B 5/6898; H04L 67/10; H04L 67/12; G06F 9/4843
See application file for complete search history.

(56) References Cited

U.S. PATENT DOCUMENTS

| | | | | |
|---|---|---|---|---|
| 7,551,916 | B2 * | 6/2009 | Gortz | H04M 1/6505 |
| | | | | 455/412.1 |
| 2008/0139952 | A1 * | 6/2008 | Kuroda | A61B 5/02438 |
| | | | | 600/508 |

(Continued)

FOREIGN PATENT DOCUMENTS

| | | | | |
|---|---|---|---|---|
| EP | 2040214 A1 | 3/2009 | | |
| EP | 2988213 A1 * | 2/2016 | ........... | A61B 5/6898 |

(Continued)

OTHER PUBLICATIONS

"Sense and Sensor-Bility: Access Mobile Device Sensors With JavaScript", Mobiforge, Retrieved on Nov. 13, 2015, Webpage available at : https://mobiforge.com/design-development/sense-and-sensor-bility-access-mobile-device-sensors-with-javascript.

(Continued)

*Primary Examiner* — Laura M Menz
(74) *Attorney, Agent, or Firm* — Alston & Bird LLP

(57) ABSTRACT

According to one aspect there is provided a method comprising: loading, with an application, a webpage comprising an embedded activity recognition module; causing collection of activity sensor data from at least one sensor of a mobile device with a sensor polling module; causing transmission of the activity sensor data to the embedded activity recognition module; causing processing of the collected sensor data with the embedded activity recognition module to form processed activity sensor data; and receiving the processed activity sensor data from the activity recognition module.

21 Claims, 10 Drawing Sheets

(56) References Cited

U.S. PATENT DOCUMENTS

| | | | |
|---|---|---|---|
| 2011/0173130 A1* | 7/2011 | Schaefer, IV | G06Q 30/02 705/347 |
| 2011/0184791 A1* | 7/2011 | Wang | G06Q 30/02 705/14.7 |
| 2012/0136865 A1* | 5/2012 | Blom | G06F 16/173 707/739 |
| 2013/0006906 A1* | 1/2013 | Cook | G06N 5/02 706/46 |
| 2013/0173517 A1* | 7/2013 | Berus | G06N 5/02 706/45 |
| 2013/0210480 A1* | 8/2013 | Pollington | H04W 88/02 455/550.1 |
| 2013/0210577 A1* | 8/2013 | Ceoldo | A61H 7/001 482/1 |
| 2013/0218058 A1* | 8/2013 | Ceoldo | A61H 7/001 601/46 |
| 2013/0232552 A1* | 9/2013 | Brush | G06F 21/6263 726/4 |
| 2013/0310713 A1* | 11/2013 | Weber | A61B 5/0002 600/595 |
| 2013/0321425 A1* | 12/2013 | Greene | G01N 33/48 345/440 |
| 2014/0029762 A1* | 1/2014 | Xie | H04R 5/027 381/94.1 |
| 2014/0096264 A1* | 4/2014 | Root | G06F 19/3418 726/27 |
| 2015/0363802 A1* | 12/2015 | Varian | G06Q 30/0203 705/7.32 |
| 2016/0012749 A1* | 1/2016 | Connor | G09B 5/00 600/13 |
| 2016/0051199 A1* | 2/2016 | Tishutin | A61B 5/6898 702/190 |
| 2016/0140353 A1* | 5/2016 | Biswas | G06F 21/62 726/1 |
| 2016/0239084 A1* | 8/2016 | Connor | A61B 5/0478 |
| 2016/0242698 A1* | 8/2016 | Repka | A61B 5/7214 |
| 2017/0164878 A1* | 6/2017 | Connor | A61B 5/14532 |
| 2017/0171359 A1* | 6/2017 | Ando | H04Q 9/00 |

FOREIGN PATENT DOCUMENTS

| | | | | |
|---|---|---|---|---|
| EP | 2988213 A1 | * | 2/2016 | ........... A61B 5/6898 |
| RU | 2014133946 A | * | 3/2016 | ........... A61B 5/6898 |
| RU | 2014133946 A | * | 3/2016 | ........... A61B 5/6898 |
| RU | 2606880 C2 | * | 1/2017 | ........... A61B 5/6898 |
| RU | 2606880 C2 | * | 1/2017 | ........... A61B 5/6898 |
| WO | 2011/020135 A1 | | 2/2011 | |
| WO | 2013/038230 A1 | | 3/2013 | |

OTHER PUBLICATIONS

"Standards for Web Applications on Mobile: Current State and Roadmap", The World Wide Web Consortium (W3C), Retrieved on Nov. 13, 2015, Webpage available at : http://www.w3.org/2014/04/mobile-web-app-state/#User_interactions.

"Geolocation Working Group Charter", W3C Ubiquitous Web Domain, Retrieved on Nov. 13, 2015, Webpage available at : http://www.w3.org/2014/04/geo-charter.html.

"Device Orientation Event Specification", The World Wide Web Consortium (W3C), Retrieved on Nov. 13, 2015, Webpage available at : http://w3c.github.io/deviceorientation/spec-source-orientation.html.

"The Internet of Things", Armmbed, Retrieved on Nov. 13, 2015, Webpage available at : https://developer.mbed.org/cookbook/IOT.

Office action received for corresponding Russian Patent Application No. 2014133946, dated Oct. 28, 2014, 3 pages of office action and no pages of office action translation available.

Office action received for corresponding Russian Patent Application No. 2014133946, dated Nov. 30, 2015, 8 pages of office action and 4 pages of office action translation available.

Extended European Search Report received for corresponding European Patent Application No. 15180342.6, dated Jan. 25, 2016, 6 pages.

"Moves 2.0 Adds M7 Support for iPhone 5s", Moves, Retrieved on Mar. 17, 2016, Webpage available at : https://www.moves-app.com/press/moves2-launch.

Office Action for corresponding European Patent Application No. 15180342.6 dated Feb. 21, 2018, 9 pages.

Liao, L. et al., *Learning and inferring transportation routines*, Artificial Intelligence, Elsevier, vol. 171 (2007) 311-331.

* cited by examiner

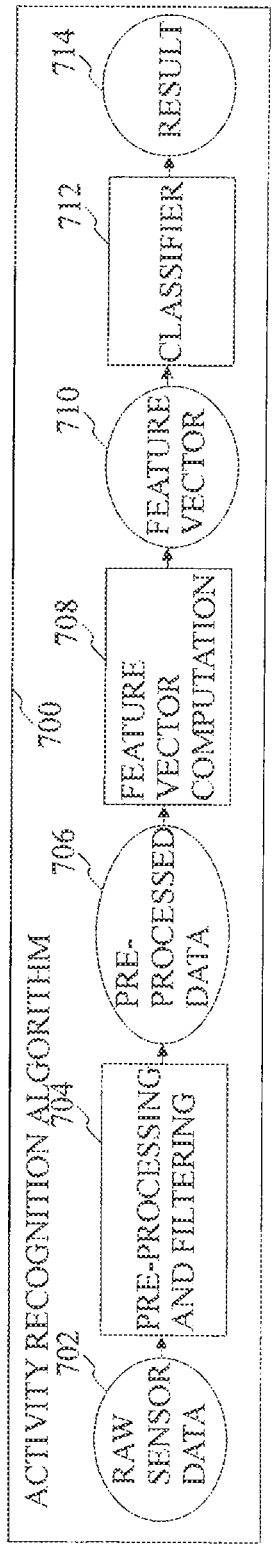
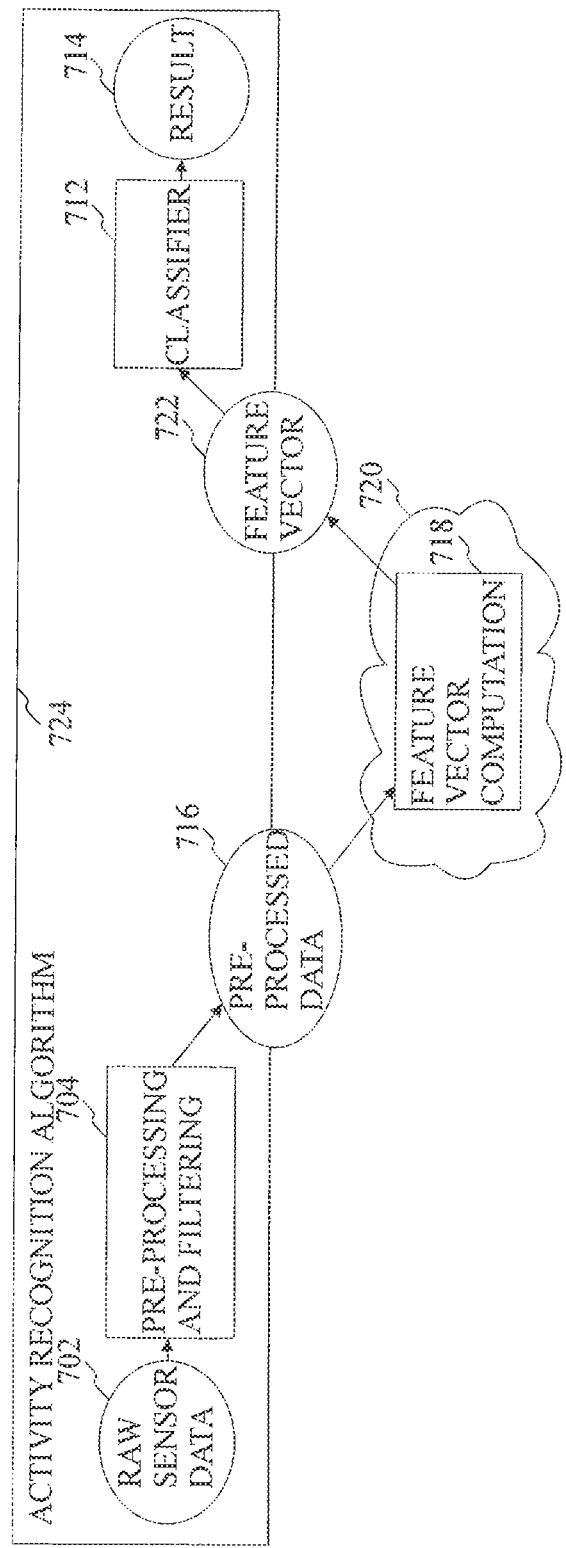
FIG. 7A
FIG. 7B

METHOD, APPARATUS AND COMPUTER PROGRAM FOR ACTIVITY SENSOR DATA PROCESSING

TECHNICAL FIELD

The present disclosure relates to the field of activity sensors, associated methods, apparatuses and computer programs. Certain disclosed aspects/embodiments relate to an electronic apparatus which provides and processes activity sensor data.

BACKGROUND

Today's portable electronic devices, for example, smartphones and wearable devices may contain multiple sensors, which enhance the user experience. Usually such device includes at least an accelerometer. The most common form of mobile computing in use today is the smartphone. These may have a number of different sensors implemented initially to improve the user experience such as using the accelerometer to measure changes in screen orientation or the magnetometer to support location and navigation applications. These sensors can also be used to collect data that helps to understand human behavior, recognize specific activities, augment human memory of events, improve sporting performance and provide support for different therapies including both body movement and sleep disorders.

There are applications for portable electronic devices that use, or could use some data regarding user's current activity that can be gathered from the sensors, but this requires from the application developers the competence and additional resources needed to develop new sensor algorithms. Program developers do not have many options of activity recognition algorithms to choose from. Either the developers create and implement their own activity recognition algorithm, or they use activity recognition algorithm of operation system, if it supplies one.

Based on the above, there is a need for a solution that would enable more efficient and versatile use of activity recognition algorithms.

SUMMARY

According to a first aspect, there is provided a method comprising loading, with an application, a webpage comprising an embedded activity recognition module; causing collection of activity sensor data from at least one sensor of a mobile device with a sensor polling module; causing transmission of the activity sensor data to the embedded activity recognition module; causing processing of the collected sensor data with the embedded activity recognition module to form processed activity sensor data; and receiving the processed activity sensor data from the activity recognition module.

According to a second aspect, there is provided an apparatus comprising at least one processor; and at least one memory having computer program code stored thereon, the at least one memory and computer program code being configured to, when run on the at least one processor, cause the apparatus to: load, with an application, a webpage comprising an embedded activity recognition module; cause collection of activity sensor data from at least one sensor of a mobile device with a sensor polling module; cause transmission of the activity sensor data to the embedded activity recognition module; cause processing of the collected sensor data with the embedded activity recognition module to form processed activity sensor data; and receive the processed activity sensor data from the activity recognition module.

According to a second aspect, there is provided an apparatus comprising means for loading a webpage comprising an embedded activity recognition module; means for causing collection of activity sensor data from at least one sensor of a mobile device with a sensor polling module; means for causing transmission of the activity sensor data to the embedded activity recognition module; means for causing processing of the collected sensor data with the embedded activity recognition module to form processed activity sensor data; and means for receiving the processed activity sensor data from the activity recognition module.

According to a second aspect, there is provided a computer program comprising code to load a webpage comprising an embedded activity recognition module; code to cause collection of activity sensor data from at least one sensor of a mobile device with a sensor polling module; code to cause transmission of the activity sensor data to the embedded activity recognition module; code to cause processing of the collected sensor data with the embedded activity recognition module to form processed activity sensor data; and code to receive the processed activity sensor data from the activity recognition module.

In one example, the webpage is loaded from a web server.

In one example, the loaded web page is stored on the mobile device.

In one example, the processing of the collected the sensor data comprises: preprocessing and filtering the activity sensor data to provide preprocessed data; computing a feature vector; and identifying user activity and/or additional statistics based on the feature vector.

In one example, the processing of the collected sensor data comprises: preprocessing and filtering the activity sensor data to provide preprocessed data; causing transmission of the preprocessed data to a network server for feature vector computation; and receiving the feature vector from the network server; and identifying user activity and/or additional statistics based on the afeature vector.

In one example, the processing of the collected sensor data comprises: preprocessing and filtering the activity sensor data to provide preprocessed data; computing a feature vector; causing transmission of the feature vector to a network server for identifying user activity and/or additional statistics based on the feature vector; and receiving user activity and/or additional statistics from the network server.

In one example, the webpage comprises the sensor polling module as an embedded the sensor polling module.

In one example, the application comprises the sensor polling module.

In one example, the embedded activity recognition algorithm is selected from a plurality of embedded activity recognition algorithms.

In one example, the embedded activity recognition module is selected from a plurality of embedded activity recognition modules and at least one activity recognition module provided by the operating system of the mobile device, third party applications or services.

In one example, at least two activity recognition modules is selected from a plurality of embedded activity recognition modules and/or activity recognition modules provided by the operating system of the mobile device, third party applications or services; and presenting results of the selected at least two activity recognition modules is caused to a user of the mobile device simultaneously.

In one example, the selecting comprises selecting the activity recognition module based on user selection, user's preferences, system preferences or by automatic selection.

In one example, collection of additional data is caused; and transmission of the additional data and/or the received processed activity sensor data is caused back to at least one activity recognition module.

In one example, transmission of at least one of the processed activity sensor data and data provided by the application is caused via a network connection.

In one example, processing of the collected sensor data comprises: causing transmission of data to a cloud service; receiving cloud service processed data from the cloud service, wherein the cloud processed data takes into account activity sensor data from at least one other device; wherein the processed activity sensor data takes into account the cloud processed data.

In one example, the loaded webpage or activity recognition module comprises multiple implementations of similar activity recognition modules being optimized to different conditions; wherein the method further comprises: selecting an activity recognition module implementation matching best to the current condition with the mobile device.

In one example, the selection of the activity recognition module is made automatically, triggered by the application or in response to user selection.

In one example, the application comprises multiple implementations of similar activity recognition modules being optimized to different conditions, wherein the method further comprises: selecting, with the application, an activity recognition module implementation matching best to the current condition with the mobile device.

BRIEF DESCRIPTION OF THE DRAWINGS

The accompanying drawings, which are included to provide further understanding and constitute a part of this specification, illustrate example embodiments. In the drawings:

FIG. 7A illustrates a block diagram of an activity recognition module according to one example embodiment;

FIG. 7B illustrates a block diagram of an activity recognition module according to another example embodiment;

DETAILED DESCRIPTION

In the following, the description is illustrated at least partly using examples implemented using HTML5 and JavaScript. Activity recognition algorithms may be written in JavaScript and presented in HTML5 webpages on the internet. These webpage implementations provide documented interfaces for data exchange with external applications. Then, when an application developer writes some application that wants to use specialized activity recognition algorithms, they make use of a HTML5 webpage with the sensor algorithms into their application. However, it is to be understood that these examples are non-limiting and that example embodiments may be implemented by using any appropriate webpage format or programming language. Further, the example embodiments use the term "activity recognition algorithm" to generally refer to an activity recognition module which is an application or a program entity.

Further, sensor data used herein refers to data generated by at least one sensor of a device, for example, a mobile device. The device may have a number of different sensors, such as an accelerometer, a magnetometer, a gyroscope, a barometer, an ambient light sensor, an ambient temperature sensor, a humidity sensor, a microphone, a camera, a touchscreen etc.

Figure 1A:
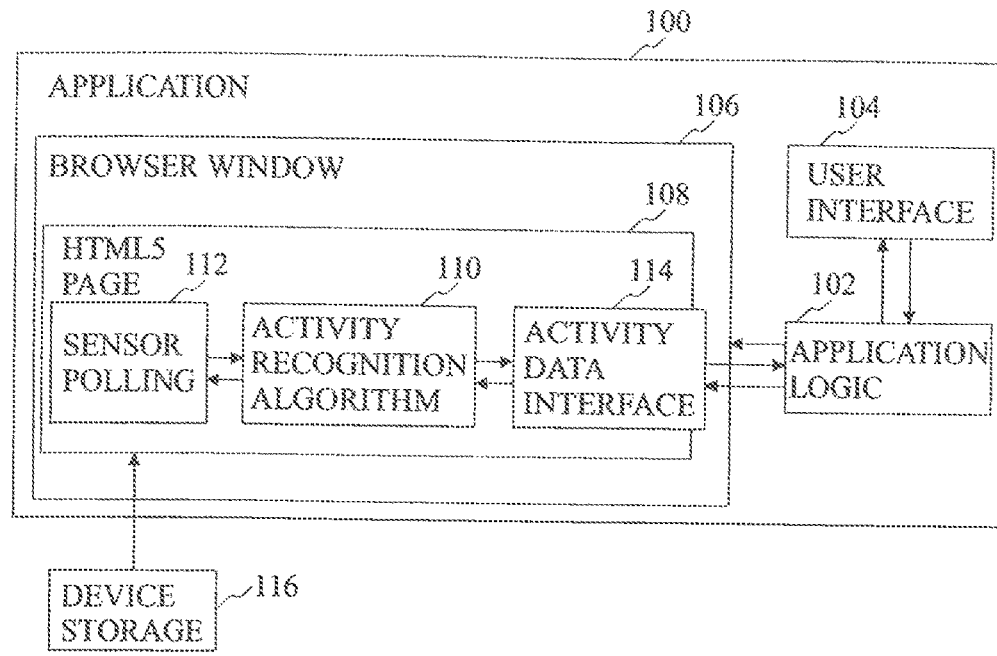
FIG. 1A illustrates a block diagram of an application according to one example embodiment.

FIG. 1A illustrates a block diagram of an application 100 according to one example embodiment. The application 100 comprises an application logic module 102 which controls the execution of the application 100. The application logic module 102 also controls representation of data in a user interface 104. When the application 100 is run, the application logic module 102 may perform some specific initialization processes. For example, the application logic module initializes a browser window 106 and loads, from a device storage 116, a desired webpage 108 comprising an embedded activity recognition algorithm. The webpage 108 may be a HTML5 webpage. The embedded activity recognition algorithm 110 refers, for example, to an activity recognition algorithm that is written in JavaScript and embedded into the HTML5 webpage. When the webpage has been loaded, the application logic module 102 initializes the activity recognition algorithm 110 through an activity data interface 114, and starts the algorithm and a sensor polling module 112. The activity data interface 114 implements special processes for data exchange between the activity recognition algorithm 110 and external applications. These processes may be different depending on the platform on which the application 100 runs. They are, for example, some platform-specific JavaScript methods for data exchange with other programs, or some platform-specific variables and objects that are accessible from other programs.

As FIG. 1A discloses, the webpage 108 comprises also the sensor polling module 112 as an embedded module or algorithm. Similarly to the activity recognition algorithm 110, also the sensor polling module 112 may be written using JavaScript. After starting the activity recognition algorithm 110 and the sensor polling module 112, they are run in the browser window 106.

The sensor polling module 112 collects sensor data from at least one sensor (not disclosed in FIG. 1A) of a mobile device running the application 100. The collected sensor data is sent to the activity recognition algorithm 110. The activity recognition algorithm 110 processes the collected sensor data and sends to the application logic module 102, through the activity data interface 114, the processed data relating to detected activity. The application logic module 102 may cause at least part of the processed data to be presented to a user of the mobile device via the user interface 104. The user may repeatedly interact with the application 100 through the user interface 104, and the application 100 may provide the user with information about user's present and past activities and other relevant information.

In the example embodiment described above, no connectivity (to, for example, the Internet) is needed after the application 100 has been installed on the user's device since the webpage 108 comprising the embedded modules is stored on the device storage 116.

Figure 1B:
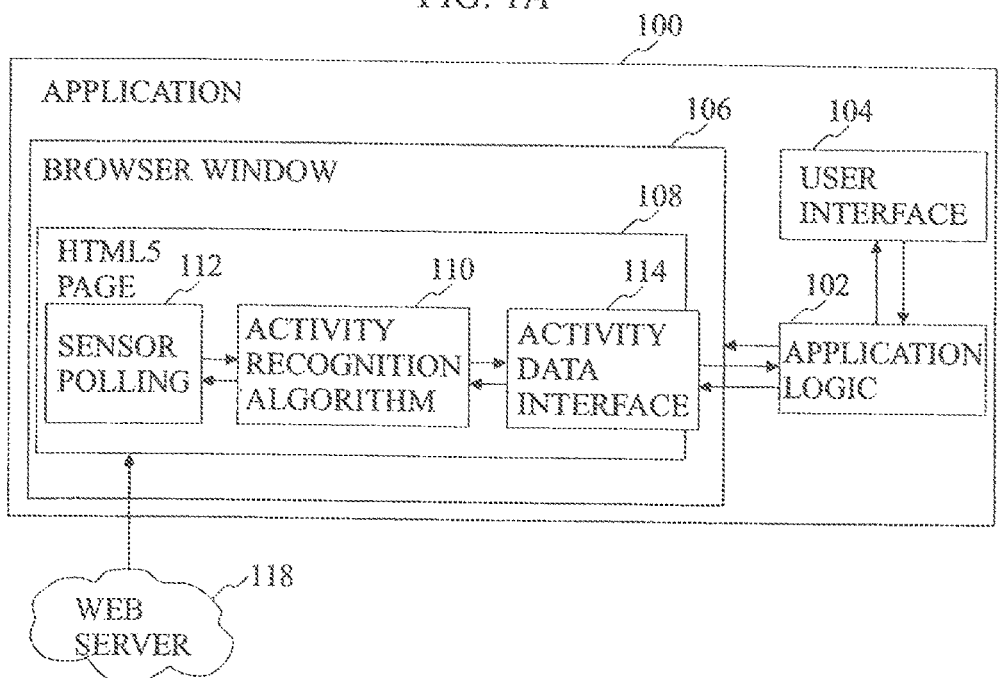
FIG. 1B illustrates a block diagram of an application according to another example embodiment.

FIG. 1B illustrates a block diagram of an application 100 according to another example embodiment. The example embodiment disclosed in FIG. 1B is similar with the example embodiment disclosed in FIG. 1A with the exception that the application 100 loads the webpage 106 from a web server 118 and may update it frequently enough to ensure that the latest version of the activity recognition algorithm is used.

In a further example embodiment with reference to example embodiments disclosed in FIGS. 1A and 1B, the application 100 may cache the webpage 108 loaded on the device, so that it can be used even when there is no connectivity. The cache may have a controlled lifetime and may be erased at the end of this lifetime to make unauthorized copying of the cache impossible and to prevent the application from using the older version of the algorithm.

Figure 2:
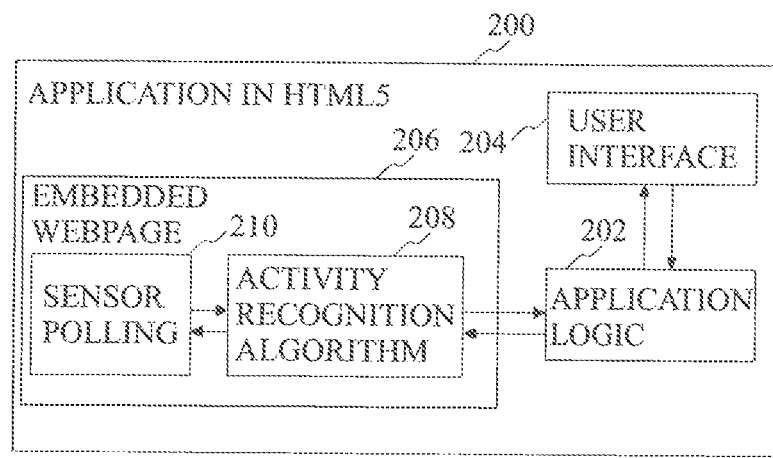
FIG. 2 illustrates a block diagram of an application according to another example embodiment.

FIG. 2 illustrates a block diagram of an application according to another example embodiment. The application 200 comprises an application logic module 202 which controls the execution of the application 200. The application logic module 202 also controls representation of data in a user interface 204.

In this example embodiment, the application 200 itself is written in HTML5 and JavaScript and is a webpage running in a browser, in a Web View in another application, or is run inside an application automatically generated by a cross-platform framework (for example, PhoneGap). Alternatively, the operation system may allow running HTML5 pages as applications (like Firefox OS, Chrome OS, etc.). In this case the HTML5 page containing the algorithm may be embedded into the application using means of HTML5, for example, iframe.

The embedded webpage 206 comprises an activity recognition algorithm 208 and a sensor polling module 210. The activity recognition algorithm 208 and the sensor polling module 210 may be written using JavaScript. The sensor polling module 210 collects sensor data from at least one sensor (not disclosed in FIG. 2) of a mobile device running the application 200. The collected sensor data is sent to the activity recognition algorithm 208. The activity recognition algorithm 208 processes the collected sensor data and sends to the application logic module 202 processed data relating to detected activity. The application logic module 202 may cause at least part of the processed data to be presented to a user of the mobile device via the user interface 204. The user may repeatedly interact with the application 200 through the user interface 204, and the application 200 may provide the user with information about user's present and past activities and other relevant information.

Figure 3:
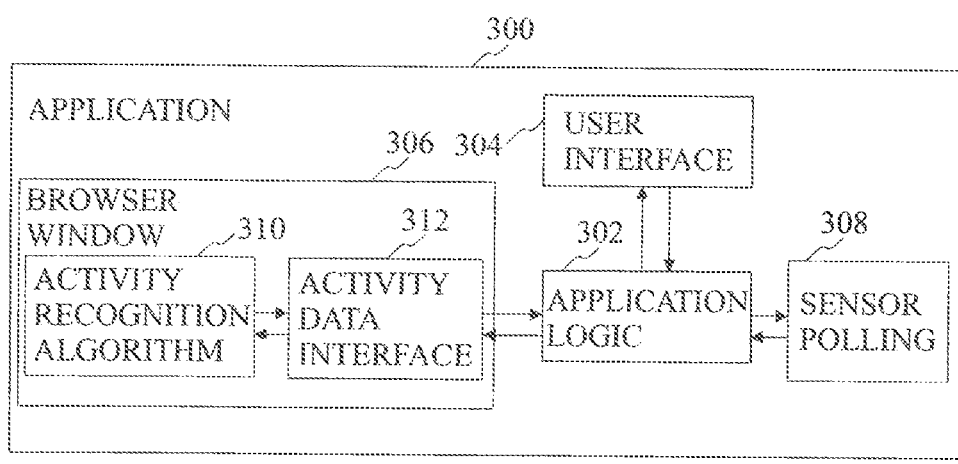
FIG. 3 illustrates a block diagram of an application according to another example embodiment.

FIG. 3 illustrates a block diagram of an application according to another example embodiment. The application 300 comprises an application logic module 302 which controls the execution of the application 300. The application logic module 302 also controls representation of data in a user interface 304. When the application 300 is run, the application logic module 302 may perform some specific initialization processes. For example, the application logic module initializes a browser window 306 and loads, from device storage or from the internet, a desired webpage 306 comprising an embedded activity recognition algorithm 310. The webpage 306 may be a HTML5 webpage. The embedded activity recognition algorithm 306 refers, for example, to an activity recognition algorithm that is written in JavaScript and embedded into the HTML5 webpage. When the webpage has been loaded, the application logic module 302 initializes the activity recognition algorithm 310 through an activity data interface 312, and starts the algorithm. After starting the activity recognition algorithm 310, it is run in the browser window 306.

The activity data interface 312 implements special processes for data exchange between the activity recognition algorithm 310 and external applications. These processes may be different depending on the platform on which the application 300 runs. They are, for example, some platform-specific JavaScript methods for data exchange with other programs, or some platform-specific variables and objects that are accessible from other programs.

As FIG. 3 discloses, the application 300 comprises also a sensor polling module 308. The application logic module 302 also starts the sensor polling module 308, and after starting, the sensor polling module 308 collects sensor data from at least one sensor (not disclosed in FIG. 3 of a mobile device running the application 300. The collected sensor data is sent to the activity recognition algorithm 310 through the activity data interface 312. The activity recognition algorithm 310 processes the collected sensor data and sends to the application logic module 302, through the activity data interface 312, processed data relating to detected activity. The application logic module 302 may cause at least part of the processed data to be presented to a user of the mobile device via the user interface 304. The user may repeatedly interact with the application 300 through the user interface 304, and the application 300 may provide the user with information about user's present and past activities and other relevant information.

Figure 4:
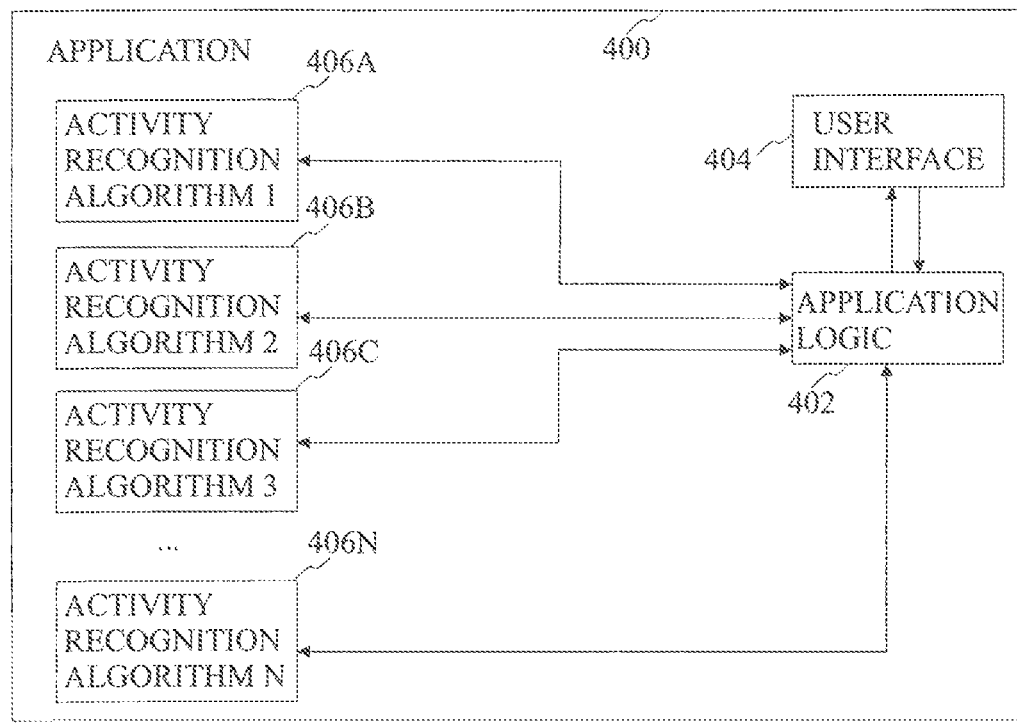
FIG. 4 illustrates a block diagram of an application according to another example embodiment.

FIG. 4 illustrates a block diagram of an application according to another example embodiment. The example embodiment of FIG. 4 is similar to the example embodiments disclosed above with the exception there is more than one activity recognition algorithm that can be used. All activity recognition algorithms 406A, 406B, 406C, 406N may be implemented as a HTML5 webpage and JavaScript code available to application 400.

In FIG. 4 activity recognition algorithms 406A, 406B, 406C, 406N are configured to collect sensor data from at least one sensor (not disclosed in FIG. 4) of a mobile device running the application 400. The activity recognition algorithms 406A, 406B, 406C, 406N process the collected sensor data and send the processed data to the application logic module 402.

The application 400 may be configured to allow a user to select via the user interface the best algorithm from a library or database of available activity recognition algorithms, for example, based on user's current preferences or the system's preferences (depending on the arrangement of the system). Alternatively, the application 400 may select the best algorithm automatically. Alternatively, the application 400 may present to the user results of one, or more, or all activity recognition algorithms running simultaneously in parallel.

In a further example embodiment of FIG. 4, the application 400 may also use activity recognition algorithms implemented by the operation system of the mobile device or provided by other third parties.

In a further example embodiment of FIG. 4, the application 400 may provide additional data from various sources to the activity recognition algorithm via the application logic module 402 in order to improve algorithm performance as measured, for example, by speed of computation, accuracy, precision and relevance of the results to the user etc. Further, this additional data may include results of work of other activity recognition algorithms that run in parallel, or information about user's selection of one algorithm or another, or information of other user's actions within the application 400, or information of user explicitly specifying his current and past activities, or user's unique identifier or other information available on the web or from the device that is pertinent to the analysis being performed by the activity recognition algorithm.

Additionally, the activity recognition algorithm or algorithms 406A, 406B, 406C, 406N not only process data but may also send to the internet (for example, to a cloud service) both data and results in order to improve current and future performance quality of the algorithm. Further, the activity recognition algorithm or algorithms 406A, 406B, 406C, 406N may obtain from the internet (for example, cloud service) some additional information that can improve current and future performance quality of the activity recognition algorithm or algorithms 406A, 406B, 406C, 406N. Data may be further analyzed by algorithm developers and new, improved version of algorithm is released, or may be data is analyzed automatically and corrections to algorithm results are generated and sent back to algorithm automatically.

Figure 5:
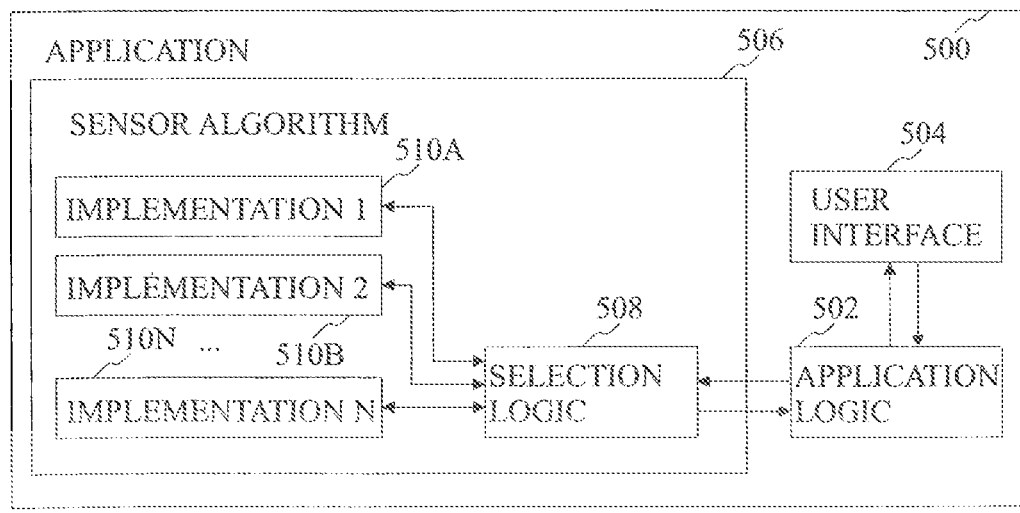
FIG. 5 illustrates a block diagram of an application according to another example embodiment.

FIG. 5 illustrates a block diagram of an application according to another example embodiment. The example embodiment of FIG. 5 is similar to the example embodiments disclosed above with the exception that the webpage or JavaScript code 506 of the activity recognition algorithm itself contains two or more implementations 510A, 510B, 510N of similar algorithms that require, for example, different connectivity, different computation power and different warm-up time. The webpage or JavaScript code of the algorithm 506 also contains a selection logic module 508 that allows automatic, or controlled by user or application, switching between the variety of implementations 510A, 510B, 510N, for example, based on current connectivity, available power, amount of data collected so far etc.

For example, when the application 500 has just started, the implementation 510A, 510B, 510N version that needs no initial data is activated and it analyses the first sensor data, then, after some amount of data is collected, a more precise or relevant version of the algorithm is switched on. When connectivity to the internet is lost, an autonomous version may be switched on. Further, when device is short on battery power, the less precise but less power-hungry version of the algorithm may be switched on. The switching may happen automatically and be totally hidden from the application developer or user. Alternatively, a control approach may be used where the change in the implementation selection may be triggered by the application 500 or the user.

Figure 6:
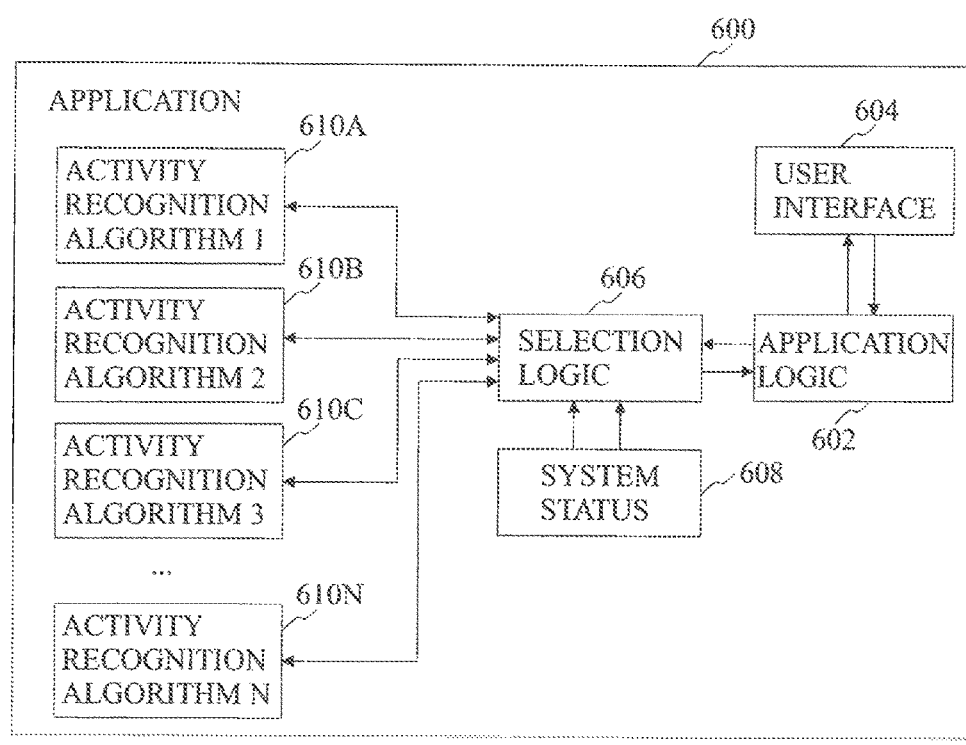
FIG. 6 illustrates a block diagram of an application according to another example embodiment.

FIG. 6 illustrates a block diagram of an application 600 according to another example embodiment. The example embodiment of FIG. 6 is similar to the example embodiments disclosed above with the exception that the application comprises a plurality of activity recognition algorithms 610A, 610B, 610C, 610N. The application logic module 602 controls a selection logic module 606 in selecting one of the activity recognition algorithms 610A, 610B, 610C, 610N based on system status 608 information. The system status information refers, for example, to current connectivity to the Internet, available power, amount of data collected so far etc. Further, the selection logic module 606 may also switch between the variety of implemented activity recognition algorithms based on the status information 608. The application logic module 602 also controls representation of processed activity sensor data in a user interface 604. FIG. 7A illustrates a block diagram of an activity recognition algorithm 700 according to one example embodiment. In this example embodiment, the activity recognition algorithm 700 consists of multiple stages of sensor signal processing.

Raw sensor data 702 is pre-processed and filtered at 704 resulting in pre-processed data 706. A feature vector or vectors is computed based on pre-processed sensor data 706 at 708 resulting in the feature vector 710. A classifier 712 uses the feature 710 vector to identify user's activity and additional statistics relating to the user's activity resulting in the result 714. The result 714 may then be sent back to the application, and the application is able to provide the user with statistics via a user interface.

FIG. 7B illustrates a block diagram of an activity recognition algorithm 724 according to another example embodiment. The example embodiment disclosed in FIG. 7B differs from the example embodiment of FIG. 7A in that some of the processing is performed as a cloud service 720.

The pre-processing 704 of data is run by the activity recognition algorithm 724, and the activity recognition algorithm sends the pre-processed data 716 to the cloud service 720 for feature vector computation 718. When the feature vector has been computer, the cloud service 720 sends the feature vector 722 back to the activity recognition algorithm 724.

This embodiment enables, for example, the protection of proprietary steps in the algorithm as they are never downloaded to the mobile device. If this information is kept in the cloud service this protects the proprietary data from copying on the mobile device.

Figure 7C:
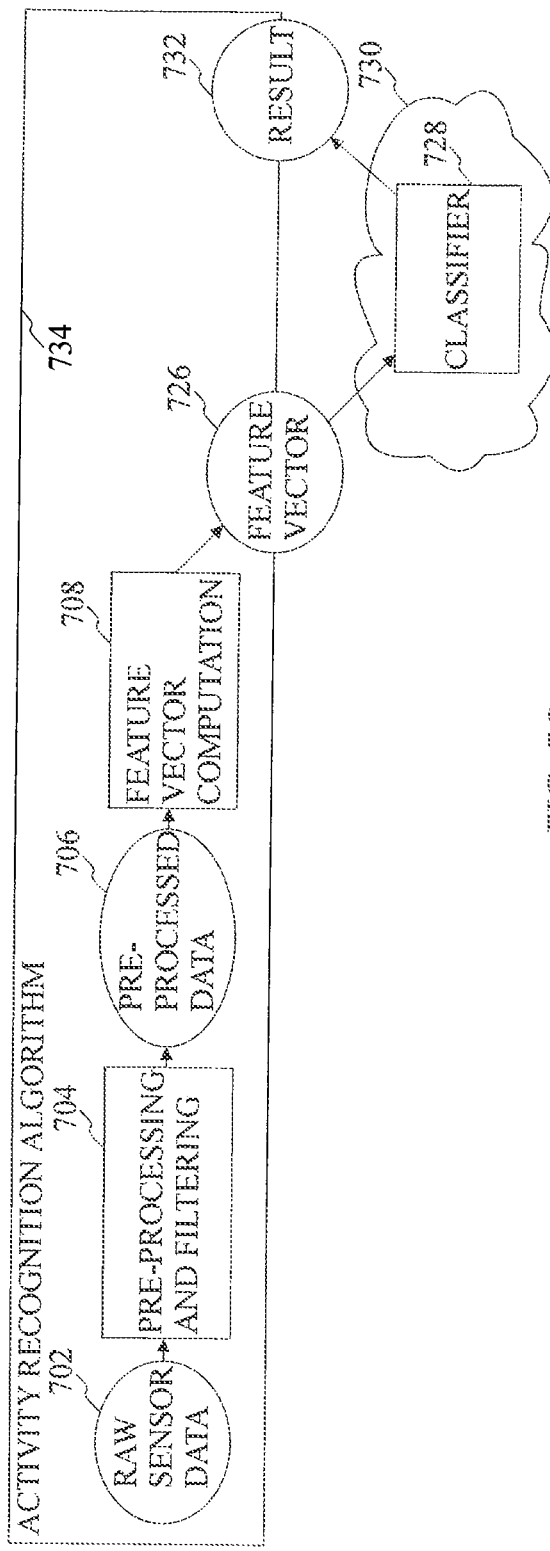
FIG. 7C illustrates a block diagram of an activity recognition module according to another example embodiment.

FIG. 7C illustrates a block diagram of an activity recognition algorithm 734 according to another example embodiment. The example embodiment disclosed in FIG. 7C differs from the example embodiment of FIG. 7A in that some of the processing is performed as a cloud service 730.

The pre-processing 704 of data and the feature vector computation 708 are run by the activity recognition algorithm 734, and the activity recognition algorithm 734 sends the feature vector 726 to the cloud service 730 for classifying with a classifier 728. The classifier 730 sends the result 732 back to the activity recognition algorithm 734.

The solution disclosed in FIG. 7C may be useful to minimize data transfer, since the feature vector and classification result need significantly less space than raw or preprocessed data. Further, this embodiment enables, for example, the protection of proprietary steps in the algorithm as they are never downloaded to the mobile device. If this information is kept in the cloud service this protects the proprietary data from copying on the mobile device.

Further to FIGS. 7A, 7B and 7C, the following gives some examples what preprocessing and signal filtering, feature vector computation and classifier may include.

Regarding signal filtering, an input signal may be filtered for noise suppression and enhancement of useful signal or useful frequencies. Also excessive information may be removed by filtering in order to compress signal. One example of signal filtering is downsampling of the input signal.

Another example of signal filtering is application of convolution filter, or finite impulse response (FIR) filter, which outputs the sum (convolution) of the finite number of previous signal samples multiplied by predefined weights. The simplest example of such a filter is a moving average filter that, for given finite natural number N, outputs average of last N input signal samples.

Another example of signal filtering is application of infinite response filter (IIR), which, for given natural numbers M and N, outputs the weighted sum of M previous output signal samples plus the weighted sum of N previous input signal samples.

Another example of signal filtering is computing number of numerical derivatives or integrals of input signal or applying linear filters with specific frequency transformation (which can be proven to be equivalent to either FIR or IIR filters).

Another example of signal filtering is application of non-linear filters, for example median filter, which, for given natural number N, outputs the median of last N input signal samples.

More complex filters, like Savitzky-Golay filter or Kalman filter, may also be used. Sensor fusion, for example computation of the device orientation quaternion, based on readings from more than one sensor, using Kalman filter or complementary filter, may also be done in preprocessing and filtering step. It is impossible to list all the known filters, but usually it is well known to the person skilled in the art of signal processing.

Regarding feature vector computation, features are specific characteristics extracted from the input signal that are later used by classifier to distinguish different classes of signals. For sensor signals, for example accelerometer, features can be computed for raw signal components as well as for signal magnitude, squared magnitude, signal absolute value, signal vector orientation angles.

Features may be typical statistic features like time-average, dispersion, standard deviation, quantiles and histogram values.

Features may be mathematical sample moments of various degree and properties like simple moments, central sampled moments, normalized moments. One example of such feature is skewness which is the $3^{rd}$ central moment of the signal. Another example of such feature is kurtosis which is the $4^{th}$ central moment of the signal.

Another example of the features is vector of coefficients of input signal as projected to some specific basis or filtered by a family of filters. Such features may be Fourier spectrum coefficients, cepstrum coefficients, mel-frequency cepstrum coefficients.

Features may also use more than one signal component from the same sensor or a variety of sensors, for example mixed moments like covariance, coskewness and cokurtosis.

Regarding the classifier, the classifier uses features from signal's feature vector to identify the class of the signal. Usually, classifier is described by some computation model and a set of variable parameters. Values of classifier's variable parameters are determined during the learning phase and then fixed for the working phase.

Examples of classifiers are naive Bayes classifier, decision trees, k-nearest-neighbors, support vector machine, neural networks. Further, classifiers may be grouped into committees and operated using sophisticated voting techniques and learned with advances techniques such as boosting, for example AdaBoost.

Figure 8A:
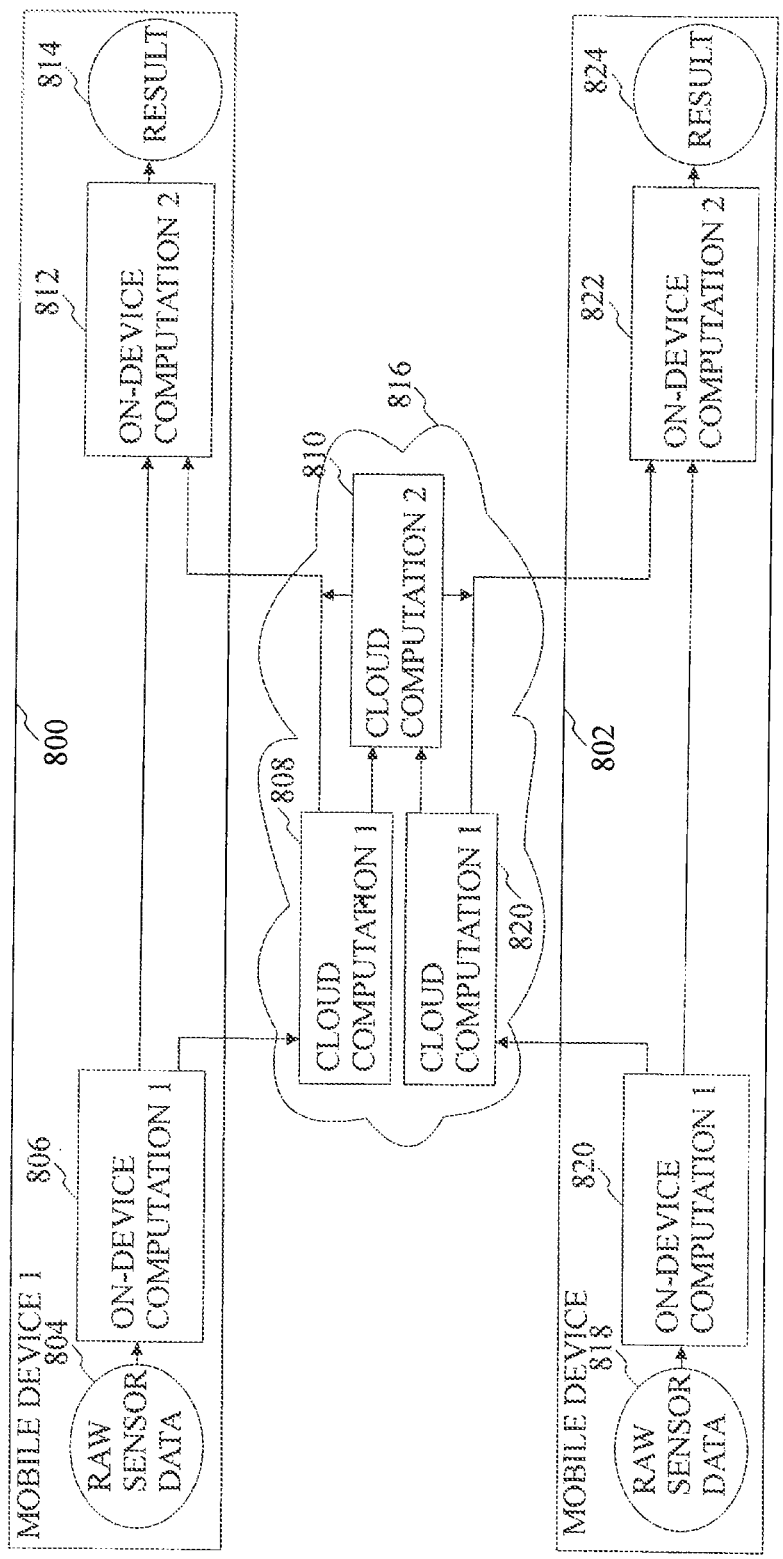
FIG. 8A discloses a block diagram illustrating the processing of sensor data according to one example embodiment.

FIG. 8A discloses a block diagram illustrating the processing of sensor data according to one example embodiment. FIG. 8A shows two mobile devices 800, 802 which are both configured to process activity sensor data at least partly. The mobile device 800 comprises an activity recognition algorithm that is configured to perform at least some of the processing disclosed in FIG. 7A. In this example embodiment, more than one device belonging to the same user or different users but linked by the need of one application to use the sensor data from all of these devices, are sending data to a cloud service 816. Part of the algorithm running in the cloud service 816 takes into consideration all available data in order to generate more precise results and send both data and/or results back to the mobile devices.

At on-device computation 806 the activity recognition algorithm processes raw sensor data 804 are least partly. The activity recognition algorithm in the mobile device 800 may send the partially processed sensor data to the cloud service 816 for cloud computation 808. Another possibility is that an application comprising the activity recognition algorithm embedded in it (for example, an activity recognition algorithm discussed in the description of FIG. 2 or 3) sends the partially processed sensor data to the cloud service 816 for cloud computation 808. Similarly, at on-device computation 820 the activity recognition algorithm processes raw sensor data 818 are least partly. The activity recognition algorithm in the mobile device 802 may send the partially processed sensor data to the cloud service 816 for cloud computation 820. Another possibility is that an application comprising the activity recognition algorithm embedded in it (for example, an activity recognition algorithm discussed in the description of FIG. 2 or 3) sends the partially processed sensor data to the cloud service 816 for cloud computation 820. Cloud computation 810 may provide further computations to the computation results from the cloud computations 808 and 820. The computation results from the cloud service 816 are sent back to the mobile device 800 or to both mobile devices 800, 802. At on-device computation 812 the webpage algorithm or the application incorporation an algorithm in the mobile device 800 takes into account data received from the cloud service 816 when computing the result 814. Similarly, at on-device computation 822 the webpage algorithm or the application incorporation an algorithm in the mobile device 802 takes into account data received from the cloud service 816 when computing the result 824.

As a summary of the example embodiment of FIG. 8A, the solution is extended to cover a situation when the user is using multiple devices in parallel or when data from a device of another user is to be taken into account, where on more than one of the devices in use a HTML5 web page containing an activity recognition algorithm that obtains unique user information and sends to the cloud service all or part of this data labelled with a unique identifier specific to the user. Some part of the algorithm that runs in the cloud takes into consideration data from all the devices in order to increase algorithms' performance quality, and sends the result back to appropriate interfaces on the devices.

Figure 8B:
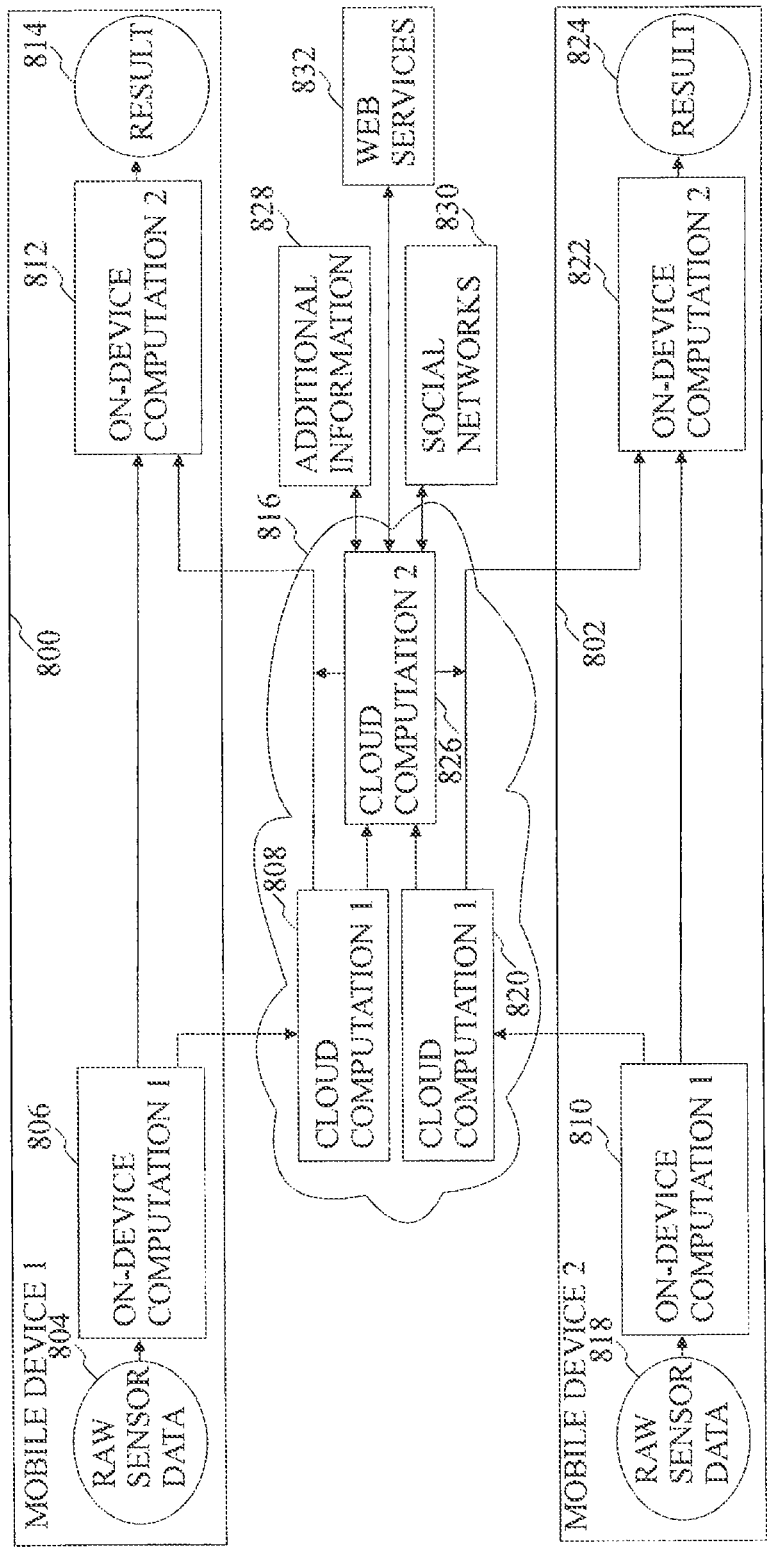
FIG. 8B discloses a block diagram illustrating the processing of sensor data according to another example embodiment.

FIG. 8B shows two mobile devices 800, 802 which are both configured to process activity sensor data at least partly. The mobile device 800 comprises an activity recognition algorithm that is configured to perform at least some of the processing disclosed in FIG. 7A. In this example embodiment, more than one device belonging to the same user or different users but linked by the need of one application to use the sensor data from all of these devices, are sending data to a cloud service 816 and then part of the algorithm running in the cloud service 816 takes into consideration all available data in order to generate more precise results and send both data and/or results back to the mobile devices.

The example embodiment of FIG. 8B differs from the example embodiment of FIG. 8A in that in FIG. 8B, the cloud computation at 826 may take into consideration information also from other sources 828, 830, 832, for example, about the user, immediate context database contents, profile on social network, search history and web visit history, on-line and real-life activities or other data sources in order to further improve algorithm performance quality. For example, if the user is clearly identified and has given permission for the system to draw on other data sources, then the algorithm may use information on user's search history or social network profile in order to improve activity prediction quality.

In one example embodiment some or all data transactions and activity recognition sensor and/or sensor polling algorithm codes in one or more of the above described example embodiments may are obfuscated, encrypted or protected in any other way. Usually webpages and embedded JavaScript code are transmitted in open and readable way. By obfuscating, encrypting or protecting in any other way the data or code unauthorized copying can be prevented.

Figure 9A:
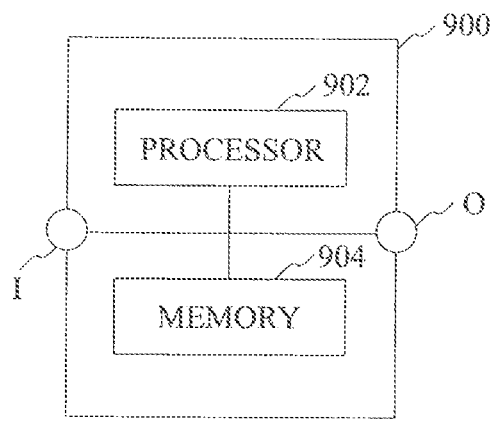
FIG. 9A illustrates a block diagram of an apparatus according to an example embodiment.

FIG. 9A shows an apparatus 900 comprising a processor 902, memory 904, input I and output O. In this embodiment only one processor and one memory are shown but it will be appreciated that other embodiments may utilize more than one processor and/or more than one memory (for example, same or different processor/memory types). The apparatus 900 may be an application specific integrated circuit (ASIC) for a portable electronic device. The apparatus 900 may also be a module for a device, or may be the device itself, wherein the processor 902 is a general purpose CPU and the memory 904 is general purpose memory. The input I allows for receipt of signaling to the apparatus 900 from further components. The output O allows for onward provision of signaling from the apparatus 900 to further components. In this embodiment the input I and output O are part of a connection bus that allows for connection of the apparatus 900 to further components. The processor 902 may be a general purpose processor dedicated to executing/processing information received via the input I in accordance with instructions stored in the form of computer program code on the memory 904. The output signaling generated by such operations from the processor 902 is provided onwards to further components via the output O.

The memory 904 (not necessarily a single memory unit) is a computer readable medium (such as solid state memory, a hard drive, ROM, RAM, Flash or other memory) that stores computer program code. This computer program code stores instructions that are executable by the processor 902, when the program code is run on the processor 902. The internal connections between the memory 904 and the processor 902 can be understood to provide active coupling between the processor 902 and the memory 904 to allow the processor 902 to access the computer program code stored on the memory 904.

Figure 9B:
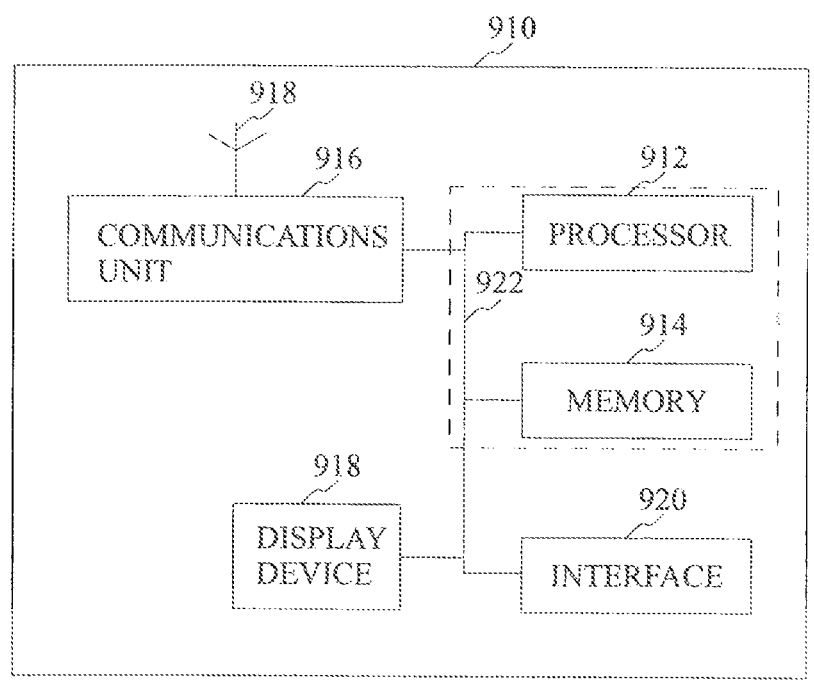
FIG. 9B illustrates a block diagram of an apparatus according to another example embodiment.

In this embodiment the input I, output O, processor 902 and memory 904 are electrically connected internally to allow for communication between the respective components I, O, 902, 904, which in this example are located proximate to one another as an ASIC. In this way the components I, O, 902, 904 may be integrated in a single chip/circuit for installation in an electronic device. In other embodiments, one or more or all of the components may be located separately (for example, throughout a portable electronic device). One or more examples of the apparatus 900 can be used as a component for another apparatus as in FIG. 9B, which shows a variation of apparatus 900 incorporating the functionality of apparatus 900 over separate components. In other examples the device 910 may comprise apparatus 900 as a module (shown by the optional dashed line box) for a mobile phone or PDA or audio/video player or the like. Such a module, apparatus or device may just comprise a suitably configured memory and processor.

The example apparatus/device 910 comprises a display 918 such as, a Liquid Crystal Display (LCD), e-Ink, or touch-screen user interface (like a tablet PC). The device 910 is configured such that it may receive, include, and/or otherwise access data. For example, device 910 comprises a communications unit 916 (such as a receiver, transmitter, and/or transceiver), in communication with an antenna 918 for connection to a wireless network and/or a port (not shown). Device 910 comprises a memory 914 for storing data, which may be received via antenna 918 or user interface 920. The processor 912 may receive data from the user interface 920, from the memory 914, or from the communication unit 916. Data may be output to a user of device 910 via the display device 918, and/or any other output devices provided with apparatus. The processor 912 may also store the data for later user in the memory 914. The device contains components connected via a communications bus 922.

The communications unit 916 can be, for example, a receiver, transmitter, and/or transceiver, that is in communication with an antenna 918 for connecting to a wireless network and/or a port (not shown) for accepting a physical connection to a network, such that data may be received via one or more types of network. The communications (or data) bus 922 may provide active coupling between the processor 912 and the memory (or storage medium) 914 to allow the processor 912 to access the computer program code stored on the memory 914.

The memory 914 comprises computer program code in the same way as the memory 904 of apparatus 900, but may also comprise other data. The processor 912 may receive data from the user interface 920, from the memory 914, or from the communication unit 916. Regardless of the origin of the data, these data may be outputted to a user of device 910 via the display device 918, and/or any other output devices provided with apparatus. The processor 912 may also store the data for later user in the memory 914.

Figure 10:
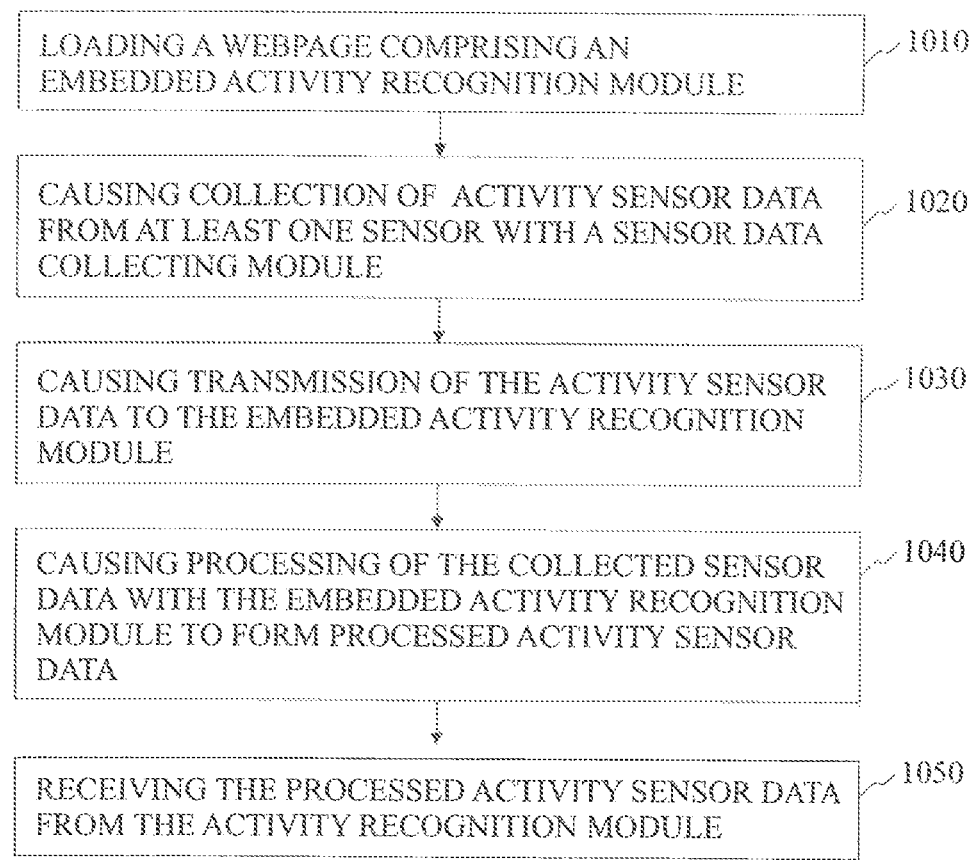
FIG. 10 illustrates a signaling block diagram of a method according to one example embodiment.

FIG. 10 illustrates a signaling block diagram of a method according to one example embodiment. The method comprises loading, a webpage comprising an embedded activity recognition module (at 1010); causing collection of activity sensor data from at least one sensor of a mobile device with a sensor polling module (at 1020); causing transmission of the activity sensor data to the embedded activity recognition module (at 1030); causing processing of the collected sensor data with the embedded activity recognition module to form processed activity sensor data (at 1040); and receiving the processed activity sensor data from the activity recognition module (at 1050). One or more of the above steps may be performed by an application running on an apparatus.

In the above described example embodiments, the application may allow the user to choose or type in the URL (Uniform Resource Locator) address of the webpage with the algorithm, or choose from some predefined set of pages. In another example, the application may open a webpage that contains not one but multiple algorithms and the user may choose the algorithm he wants. This webpage with variety of algorithms may be a marketplace that offers algorithms for use. Moreover, similar activity recognition algorithms may be built into different web-pages with different addresses in order to be used from different platforms or in different scenarios that are described above. This way algorithm remains the same, but it is just packaged in a variety of ways.

It is to be understood that the above disclosed example embodiment are only examples. In other variants, sensor algorithm may contain other blocks and other combinations of blocks may be run on the device and in the cloud, depending on current needs.

Without in any way limiting the scope, interpretation, or application of the claims appearing below, a technical effect of one or more of the example embodiments disclosed herein is that it provides an approach to improving the quantity, quality and value of the information that can be collected from any consumer device using sensors, connectivity and a web browser, and interpreting the sensor data to make it more immediately relevant to the user's needs.

Further, without in any way limiting the scope, interpretation, or application of the claims appearing below, a technical effect of one or more of the example embodiments disclosed herein is that it allows developers of cross-platform applications to use the same activity recognition algorithm on all platforms, even when a platform do not have its own built in activity recognition algorithm. Further, when webpage comprising an activity recognition algorithm is loaded from the internet, it allows automatic refresh of the algorithm if it is modified by its developers. Thus, the mobile device always uses the most current version of the algorithm.

Further, without in any way limiting the scope, interpretation, or application of the claims appearing below, a technical effect of one or more of the example embodiments disclosed herein is that it allows decoupling competence in design and development of applications and design of good user interface from competence in development of sensor algorithms. The example embodiments also provide a readily available activity sensor algorithm framework for application developers. This will increase the number of developers using the platform and so the attractiveness to the customer. Moreover, application developers who are not skilled in activity recognition algorithm development will still be able to choose and embed best activity recognition algorithm in their application.

Further, without in any way limiting the scope, interpretation, or application of the claims appearing below, a technical effect of one or more of the example embodiments disclosed herein is that it enables appearance of an algorithm marketplace, similar to application marketplaces. This in turn stimulates development of better activity recognition algorithms and better applications that use sensor algorithms.

Further, without in any way limiting the scope, interpretation, or application of the claims appearing below, a technical effect of one or more of the example embodiments disclosed herein is that it allows application developers and users to select the activity recognition algorithm from a variety of options, or even change the selection in response to changing plans or circumstances.

The example embodiments can include any suitable handheld devices, cellular telephones, smart phones, wireless devices, servers, workstations, and the like, capable of performing the methods of the example embodiments. The devices and subsystems of the example embodiments can communicate with each other using any suitable protocol and can be implemented using one or more programmed computer systems or devices.

Example embodiments may be implemented in software, hardware, application logic or a combination of software, hardware and application logic. The example embodiments can store information relating to various methods described herein. This information can be stored in one or more memories, such as a hard disk, optical disk, magneto-optical disk, RAM, and the like. One or more databases can store the information used to implement the example embodiments. The databases can be organized using data structures (e.g., records, tables, arrays, fields, graphs, trees, lists, and the like) included in one or more memories or storage devices listed herein. The methods described with respect to the example embodiments can include appropriate data structures for storing data collected and/or generated by the methods of the devices and subsystems of the example embodiments in one or more databases.

All or a portion of the example embodiments can be conveniently implemented using one or more general purpose processors, microprocessors, digital signal processors, micro-controllers, and the like, programmed according to the teachings of the example embodiments, as will be appreciated by those skilled in the computer and/or software art(s). Appropriate software can be readily prepared by programmers of ordinary skill based on the teachings of the example embodiments, as will be appreciated by those skilled in the software art. In addition, the example embodiments can be implemented by the preparation of application-specific integrated circuits or by interconnecting an appropriate network of conventional component circuits, as will be appreciated by those skilled in the electrical art(s). Thus, the example embodiments are not limited to any specific combination of hardware and/or software.

Stored on any one or on a combination of computer readable media, the example embodiments can include software for controlling the components of the example embodiments, for driving the components of the example embodiments, for enabling the components of the example embodiments to interact with a human user, and the like. Such software can include, but is not limited to, device drivers, firmware, operating systems, development tools, applications software, and the like. Such computer readable media further can include the computer program of an example embodiment for performing all or a portion (if processing is distributed) of the processing performed in implementing the example embodiments. Computer code devices of the example embodiments can include any suitable interpretable or executable code mechanism, including but not limited to scripts, interpretable programs, dynamic link libraries (DLLs), Java classes and applets, complete executable programs, and the like. Moreover, parts of the processing of the example embodiments can be distributed for better performance, reliability, cost, and the like.

As stated above, the components of the example embodiments can include computer readable medium or memories for holding instructions programmed according to the teachings and for holding data structures, tables, records, and/or other data described herein. In an example embodiment, the application logic, software or an instruction set is maintained on any one of various conventional computer-readable media. In the context of this document, a "computer-readable medium" may be any media or means that can contain, store, communicate, propagate or transport the instructions for use by or in connection with an instruction execution system, apparatus, or device, such as a computer.

A computer-readable medium may include a computer-readable storage medium that may be any media or means that can contain or store the instructions for use by or in connection with an instruction execution system, apparatus, or device, such as a computer. A computer readable medium can include any suitable medium that participates in providing instructions to a processor for execution. Such a medium can take many forms, including but not limited to, non-volatile media, volatile media, transmission media, and the like. Non-volatile media can include, for example, optical or magnetic disks, magneto-optical disks, and the like. Volatile media can include dynamic memories, and the like. Transmission media can include coaxial cables, copper wire, fiber optics, and the like. Transmission media also can take the form of acoustic, optical, electromagnetic waves, and the like, such as those generated during radio frequency (RF) communications, infrared (IR) data communications, and the like. Common forms of computer-readable media can include, for example, a floppy disk, a flexible disk, hard disk, magnetic tape, any other suitable magnetic medium, a CD-ROM, CD±R, CD±RW, DVD, DVD-RAM, DVD±RW, DVD±R, HD DVD, HD DVD-R, HD DVD-RW, HD DVD-RAM, Blu-ray Disc, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While there have been shown and described and pointed out fundamental novel features as applied to preferred embodiments thereof, it will be understood that various omissions and substitutions and changes in the form and details of the devices and methods described may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiments may be incorporated in any other disclosed or described or suggested form or embodiment as a general matter of design choice. Furthermore, in the claims means-plus-function clauses are intended to cover the structures described herein as performing the recited function and not only structural equivalents, but also equivalent structures.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed aspects/embodiments may consist of any such individual feature or combination of features. In view of the foregoing description it will be evident to a person skilled in the art that various modifications may be made within the scope of the disclosure.

The invention claimed is:

1. An apparatus comprising:
   at least one processor; and
   at least one memory having computer program code stored thereon, the at least one memory and computer program code being configured to, when run on the at least one processor, cause the apparatus to:
   load, with an application, a webpage comprising an embedded activity recognition module comprising a plurality of activity recognition algorithms or a plurality of implementations of an activity recognition algorithm;
   in response to information provided by the application, select a respective activity recognition algorithm or a respective implementation of the activity recognition algorithm based upon one or more factors including network connectivity, wherein a first version of the respective activity recognition algorithm or a first version of the respective implementation of the activity recognition algorithm is selected based upon a first network connectivity condition, and wherein the apparatus is caused to switch from the first version of the respective activity recognition algorithm or the first version of the respective implementation of the activity recognition algorithm to a second version of the respective activity recognition algorithm or a second version of the respective implementation of the activity recognition algorithm based upon a change from the first network connectivity condition to a second network connectivity condition, the second network connectivity conditions being different from the first network connectivity condition;
   cause collection of activity sensor data from at least one sensor of a mobile device with a sensor polling module;
   cause transmission of the activity sensor data to the embedded activity recognition module;
   cause processing of the collected sensor data with the respective activity recognition algorithm or the respective implementation of the activity recognition algorithm of the embedded activity recognition module that has been selected to form processed activity sensor data; and
   receive the processed activity sensor data from the activity recognition module.

2. The apparatus according to claim 1, wherein the at least one memory and computer program code being configured to, when run on the at least one processor, cause the apparatus to:
   load the webpage from a web server.

3. The apparatus according to claim 2, wherein the at least one memory and computer program code being configured to, when run on the at least one processor, cause the apparatus to:
   store the loaded web page on the mobile device.

4. The apparatus according to claim 1, wherein the at least one memory and computer program code being configured to, when run on the at least one processor, cause the apparatus to, when processing the collected the sensor data:
   preprocess and filter the activity sensor data to provide preprocessed data;
   compute a feature vector; and
   identify user activity and/or additional statistics based on the feature vector.

5. The apparatus according to claim 1, wherein the at least one memory and computer program code being configured to, when run on the at least one processor, cause the apparatus to, when processing the collected the sensor data:
   preprocess and filter the activity sensor data to provide preprocessed data;
   cause transmission of the preprocessed data to a network server for feature vector computation;
   receive the feature vector from the network server; and identify user activity and/or additional statistics based on the feature vector.

6. The apparatus according to claim 1, wherein the at least one memory and computer program code being configured to, when run on the at least one processor, cause the apparatus to, when processing the collected the sensor data:
preprocess and filter the activity sensor data to provide preprocessed data;
compute a feature vector;
cause transmission of the feature vector to a network server for identifying user activity and/or additional statistics based on the feature vector; and
receive user activity and/or additional statistics from the network server.

7. The apparatus according to claim 1, wherein
the webpage comprises the sensor polling module as an embedded the sensor polling module.

8. The apparatus according to claim 1, wherein the application comprises the sensor polling module.

9. The apparatus according to claim 1, wherein the at least one memory and computer program code being configured to, when run on the at least one processor, cause the apparatus to:
select the embedded activity recognition module from a plurality of embedded activity recognition modules and at least one activity recognition module provided by the operating system of the mobile device, third party applications or services.

10. The apparatus according to claim 1, wherein the at least one memory and computer program code being configured to, when run on the at least one processor, cause the apparatus to:
select at least two activity recognition modules from a plurality of embedded activity recognition modules and/or activity recognition modules provided by the operating system of the mobile device, third party applications or services; and
cause presenting results of the selected at least two activity recognition modules to a user of the mobile device simultaneously.

11. The apparatus according to claim 9, wherein the at least one memory and computer program code being configured to, when run on the at least one processor, cause the apparatus to select the activity recognition module based on user selection, user's preferences, system preferences or by automatic selection.

12. The apparatus according to claim 1, wherein the at least one memory and computer program code being configured to, when run on the at least one processor, cause the apparatus to:
cause collection of additional data; and
cause transmission of the additional data and/or the received processed activity sensor data back to at least one activity recognition module.

13. The apparatus according to claim 1, wherein the at least one memory and computer program code being configured to, when run on the at least one processor, cause the apparatus to:
cause transmission of at least one of the processed activity sensor data and data provided by the application via a network connection.

14. The apparatus according to claim 1, wherein the at least one memory and computer program code being configured to, when run on the at least one processor, cause the apparatus to, when processing of the collected sensor data:
cause transmission of data to a cloud service;
receive cloud service processed data from the cloud service, wherein the cloud processed data takes into account activity sensor data from at least one other device;
wherein the processed activity sensor data takes into account the cloud processed data.

15. The apparatus according to claim 1, wherein the at least one memory and computer program code being configured to, when run on the at least one processor, cause the apparatus to select the respective implementation of the activity recognition algorithm by selecting the respective implementation of the activity recognition algorithm matching best to the current condition with the mobile device.

16. The apparatus according to claim 1, wherein the selection of the respective activity recognition algorithm or the respective implementation of the activity recognition algorithm is made automatically, triggered by the application or in response to user selection.

17. The apparatus according to claim 1, wherein the application recognition module comprises multiple implementations of the activity recognition algorithm being optimized to different conditions, wherein the at least one memory and computer program code being configured to, when run on the at least one processor, cause the apparatus to:
select, with the application, the respective implementation of the activity recognition algorithm matching best to the current condition with the mobile device.

18. A method comprising:
loading, with an application, a webpage comprising an embedded activity recognition module comprising a plurality of activity recognition algorithms or a plurality of implementations of an activity recognition algorithm;
in response to information provided by the application, selecting a respective activity recognition algorithm or a respective implementation of the activity recognition algorithm based upon one or more factors including network connectivity, wherein a first version of the respective activity recognition algorithm or a first version of the respective implementation of the activity recognition algorithm is selected based upon a first network connectivity condition and wherein a switch is caused from the first version of the respective activity recognition algorithm or the first version of the respective implementation of the activity recognition algorithm to a second version of the respective activity recognition algorithm or a second version of the respective implementation of the activity recognition algorithm based upon a change from the first network connectivity condition to a second network connectivity condition, the second network connectivity conditions being different from the first network connectivity condition;
causing collection of activity sensor data from at least one sensor of a mobile device with a sensor polling module;
causing transmission of the activity sensor data to the embedded activity recognition module;
causing processing of the collected sensor data with the respective activity recognition algorithm or the respective implementation of the activity recognition algorithm of the embedded activity recognition module that has been selected to form processed activity sensor data; and
receiving the processed activity sensor data from the activity recognition module.

19. A non-transitory computer-readable medium comprising a computer program comprising program code, which when performed by an apparatus, causes the apparatus to:
- load a webpage comprising an embedded activity recognition module comprising a plurality of activity recognition algorithms or a plurality of implementations of an activity recognition algorithm;
- in response to information provided by the application, select a respective activity recognition algorithm or a respective implementation of the activity recognition algorithm based upon one or more factors including network connectivity, wherein a first version of the respective activity recognition algorithm or a first version of the respective implementation of the activity recognition algorithm is selected based upon a first network connectivity condition and a switch is caused from the first version of the respective activity recognition algorithm or the first version of the respective implementation of the activity recognition algorithm to a second version of the respective activity recognition algorithm or a second version of the respective implementation of the activity recognition algorithm based upon a change from the first network connectivity condition to a second network connectivity condition, the second network connectivity conditions being different from the first network connectivity condition;
- cause collection of activity sensor data from at least one sensor of a mobile device with a sensor polling module;
- cause transmission of the activity sensor data to the embedded activity recognition module;
- cause processing of the collected sensor data with the respective activity recognition algorithm or the respective implementation of the activity recognition algorithm of the embedded activity recognition module that has been selected to form processed activity sensor data; and
- receive the processed activity sensor data from the activity recognition module.

20. The apparatus according to claim 1, wherein the at least one memory and computer program code are configured to, when run on the at least one processor, cause the apparatus to select the respective activity recognition algorithm or the respective implementation of the activity recognition algorithm based upon a speed of computation.

21. The apparatus according to claim 1, wherein the at least one memory and computer program code are configured to, when run on the at least one processor, cause the apparatus to select the respective activity recognition algorithm or the respective implementation of the activity recognition algorithm based upon available power, wherein one version of the respective activity recognition algorithm or one version of the respective implementation of the activity recognition algorithm is selected based upon a first level of available power, and wherein the apparatus is caused to switch from the one version of the respective activity recognition algorithm or the one version of the respective implementation of the activity recognition algorithm to another version of the respective activity recognition algorithm or another version of the respective implementation of the activity recognition algorithm based upon a change from the first level of available power to a second level of available power, the second level of available power being different from the first level of available power.

* * * * *